(12) United States Patent
Eggink et al.

(10) Patent No.: US 7,838,497 B2
(45) Date of Patent: Nov. 23, 2010

(54) PRO-ANGIOGENIC PEPTIDES

(75) Inventors: Laura L. Eggink, Scottsdale, AZ (US);
J. Kenneth Hoober, Phoenix, AZ (US)

(73) Assignee: Susavion Biosciences, Inc., Tempe, AZ (US)

( * ) Notice: Subject to any disclaimer, the term of this patent is extended or adjusted under 35 U.S.C. 154(b) by 0 days.

(21) Appl. No.: 11/955,143

(22) Filed: Dec. 12, 2007

(65) Prior Publication Data
US 2008/0233081 A1 Sep. 25, 2008

Related U.S. Application Data

(60) Provisional application No. 60/869,862, filed on Dec. 13, 2006.

(51) Int. Cl.
*A61K 38/08* (2006.01)
*C07K 7/06* (2006.01)

(52) U.S. Cl. .................. 514/17; 530/329; 530/330

(58) Field of Classification Search .................. None
See application file for complete search history.

(56) References Cited

U.S. PATENT DOCUMENTS

| | | | |
|---|---|---|---|
| 5,641,747 A | 6/1997 | Popoff et al. | |
| 5,677,276 A | 10/1997 | Dickerson et al. | |
| 5,910,310 A * | 6/1999 | Heinen et al. | 424/211.1 |
| 5,919,998 A * | 7/1999 | Bandurski et al. | 800/286 |
| 6,159,937 A | 12/2000 | Larsen et al. | |
| 6,193,981 B1 | 2/2001 | Goldstein | |
| 6,551,795 B1 | 4/2003 | Rubenfield et al. | |
| 7,105,481 B2 | 9/2006 | Uutela et al. | |
| 2003/0073637 A1 | 4/2003 | Uutela et al. | |
| 2004/0031072 A1* | 2/2004 | La Rosa et al. | 800/278 |
| 2005/0063937 A1 | 3/2005 | Li et al. | |
| 2006/0024668 A1 | 2/2006 | Hock | |
| 2006/0148093 A1 | 7/2006 | Gygi et al. | |
| 2006/0160730 A1 | 7/2006 | Cuttitta et al. | |
| 2006/0287234 A1 | 12/2006 | Breen et al. | |
| 2007/0021342 A1 | 1/2007 | Breen et al. | |
| 2007/0149475 A1 | 6/2007 | Murray et al. | |

(Continued)

FOREIGN PATENT DOCUMENTS

WO 96/40903 12/1996

(Continued)

OTHER PUBLICATIONS

PCT/US2007/087413 International Search Report dated Jul. 29, 2008.

(Continued)

*Primary Examiner*—Jeffrey E Russel
(74) *Attorney, Agent, or Firm*—Fennemore Craig, P.C.

(57) ABSTRACT

This present invention generally relates to peptides, compositions, treatment methods, and devices useful for the medical diagnosis and treatment of pathogenic disorders. More specifically, the invention relates to immunostimulatory peptides which can stimulate the production of therapeutically beneficial cytokines. The peptides of the invention can regulate the release of a specific pattern of cytokines that promote angiogenesis, and modulate the immune system of a subject, without inducing deleterious side effects such as inflammation. Therefore, the peptides have therapeutic importance, particularly with respect to wound healing and restoration of circulation to damaged tissues.

25 Claims, 2 Drawing Sheets

U.S. PATENT DOCUMENTS

| | | |
|---|---|---|
| 2007/0154448 A1 | 7/2007 | Reid et al. |
| 2008/0102076 A1 | 5/2008 | Eggink et al. |
| 2009/0041793 A1 | 2/2009 | Eggink et al. |

FOREIGN PATENT DOCUMENTS

| | | |
|---|---|---|
| WO | 00/31130 | 6/2000 |
| WO | 02/058589 | 8/2002 |
| WO | 03/091275 | 11/2003 |
| WO | 2004/011650 | 5/2004 |
| WO | 2005/087793 | 9/2005 |
| WO | WO 2005/087793 A2 * | 9/2005 |
| WO | WO 2006/105021 A2 * | 3/2006 |
| WO | 2006/063028 | 6/2006 |

OTHER PUBLICATIONS

Sarig, et al.; "Telomeric and Tetraplex DNA Binding Properties of qTBP42: A Homoloque of the CArG Box Binding Protein CBF-A"; Biochemical and Biophysical Research Communications 1997, vol. 237, No. 3, pp. 617-623.

Chargelegue et al., "A Peptide Mimic of a Protective Epitope of Respiratory Synctial Virus Selected from a Combinatorial Library Induced Virus-Neutralizing Antibodies and Reduces Viral Loan In Vivo", Journal of Virology, 72(3):2040-2046 (Mar. 1998).

Chersi et al., "Specificities of rabbit antisera to multiple antigen (MAP) peptides", Journal of Biosciences, 50 (9-10):735-738 (Sep. 1, 1995) Abstract Only.

Manki et al., "Vaccination with Multiple Antigen Peptide as Rejection Antigen Peptide in Murine Leukemia", Cancer Research, 58:1960-1964 (May 1, 1998).

Nicolaus, "Symbiotic Approach to Drug Design", Decision Making in Drug Research, pp. 173-186 (Jan. 1, 1983).

European Search Report for European patent application No. 07869233.2 dated May 11, 2010.

Supplementary European Search Report for European application No. 07871699.0 dated May 17, 2010 (8 sheets).

International Search Report for WO/2005/087793 dated Apr. 5, 2006 (6 sheets).

Written Opinion of the International Searching Authority for WO/2005/087793 dated Apr. 5, 2006 (7 sheets).

International Search Report for WO/2006/063028 dated Nov. 16, 2006 (6 sheets).

Written Opinion of the International Searching Authority for WO/2006/063028 dated Nov. 16, 2006 (9 sheets).

Written Opinion of the International Searching Authority for WO/2008/076815 dated Jul. 29, 2008 (6 sheets).

Written Opinion of the International Searching Authority for WO/2008/076824 dated Aug. 5, 2008 (6 sheets).

Ciesielski et al., "Cellular antitumor immune response to a branched lysine multiple antigenic peptide containing epitopes of a common tumor-specific antigen in a rat glioma model", Cancer Immunol Immunother, 54:107-119 (2005).

Eggink et al., "A biologically active peptide mimetic of N-acetylgalactosamine/galactose", BMC Research Notes, 2:23 (2009).

Olszewska et al., "Protection against Measles Virus-Induced Encephalitis by Anti-mimotope Antibodies: The Role of Antibody Affinity", Virology, 272(1):98-105 (Jun. 20, 2000).

* cited by examiner

```
SEQUENCE LISTING

<160> NUMBER OF SEQ ID NOS: 8

<210> SEQ ID NO 1
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 1

Trp Asn Ser Thr Leu
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 2

Asn Gln His Thr Pro Arg
1               5

<210> SEQ ID NO 3
<211> LENGTH: 4
<212> TYPE: PRT
<213> ORGANISM: Artificial Sequence
<220> FEATURE:
<223> OTHER INFORMATION: linker sequence

<400> SEQUENCE: 3

Gly Gly Gly Ser
1

<210> SEQ ID NO 4
<211> LENGTH: 8
<212> TYPE: PRT
<213> ORGANISM: Artificial Sequence
<220> FEATURE:
<223> OTHER INFORMATION: linker sequence
```

```
<400> SEQUENCE: 4

Gly Gly Gly Ser Gly Gly Gly Ser
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 5

Trp Asn Ser Thr Tyr
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 6

Tyr Asn Ser Thr Leu
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 7

Tyr Gln Pro Ser Leu
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 8

Val Gln Ala Thr Gln Ser
1               5
```

PRO-ANGIOGENIC PEPTIDES

CROSS REFERENCE TO RELATED APPLICATION

This application claims priority to the earlier provisional application entitled "Angiogenic Peptides," Ser. No. 60/869,862, filed Dec. 13, 2006, the disclosures of which are hereby incorporated herein by reference.

BACKGROUND

1. Technical Field

The present invention relates generally to the use of synthetic peptides for treating human injury, in particular, to peptides and methods that stimulate angiogenesis.

2. State of the Art

Impaired circulation is an underlying aspect of many clinically-manifested disorders including peripheral arterial disease (PAD), ischemic heart disease and chronic wounds. More than 24 million patients are afflicted with these conditions in the US, with 10 million affected by PAD alone. PAD is often a result of diabetes, which currently affects one in three adults over the age of 40 and whose incidence is expected to increase as a result of increasing obesity in the general population. Chronic wounds affect more than 6.5 million patients each year and cause significant impairment of quality of life. Even with current treatments, about 35,000 limb amputations are performed each year due to life-threatening ischemia.

Wound healing after injury occurs in three major stages. First is the hemostatic and inflammatory stage, which minimizes blood loss and recruits specific cells to the site of injury. Platelets engage the injured tissue, initiate clot formation and release growth factors during this first stage. In the second stage, recruited phagocytic cells such as macrophages and monocytes digest the injured tissue and angiogenic growth factors released by activated platelets, macrophages, and other cells bind to receptors on the surface of endothelial cells in pre-existing blood vessels. The endothelial cells then proliferate, migrate into a wound bed, and differentiate into arterial and venous vascular tissue. Finally, in a third remodeling stage, new blood vessels mature by recruiting smooth muscle cells to stabilize the vasculature architecture, whereupon blood begins to flow through the new blood vessels.

Angiogenesis, the process of growth of new blood vessels, is an essential process in wound healing and for restoring blood flow to tissues after injury. The discovery of growth factors that stimulate this process has had a major influence on medical treatment of crippling and life-threatening conditions resulting from loss of blood circulation. At least 20 growth factors have been identified that stimulate angiogenesis. The growth factor most widely studied, and used clinically, is the pro-angiogenic platelet-derived growth factor-BB (PDGF-BB). PDGF is released from many cell types including activated platelets, activated macrophages, endothelial cells, fibroblasts and tumor cells, and PDGF was approved by the FDA in December 1997 for clinical use as a topical agent for diabetic foot ulcers. A second growth factor developed for clinical use is the vascular endothelial growth factor (VEGF). Growth factors of this type and biologically active analogs are typically mid-sized proteins which can be produced by recombinant techniques (e.g. in yeast), and activation of angiogenesis by growth factors is accomplished, at least in part, by stimulation of cytokine production.

IL-8 is a cytokine that activates neutrophils and has potent chemotactic activity on neutrophils and lymphocytes. The inflammatory event at the site of infection or injury activates monocytes and macrophages, which release IL-8. Inflamed endothelial tissue also releases IL-8, which attracts neutrophils from blood into the tissue during the initial phase of the defense mechanism. The consequence is a vicious cycle of recruitment of neutrophils in response to IL-8, damage to tissues, and more production of IL-8 leading to deleterious inflammation as a side effect. In addition, neutrophils adhere to inflamed endothelial tissues through integrins secreted from the cells, and ICAM-1 can stimulate release of the integrins to which neutrophils bind, thereby increasing the level of deleterious inflammation at the site of injury even further. Increased levels of certain types of clinically deleterious cytokines, such as IL-8 and ICAM-1, at a site of infection or injury can therefore cause deleterious side effects which can hinder the process of healing.

The healing of wounds in mammalian tissue may be enhanced by the application, either alone or in combination with a cytokine and/or growth factor, of certain neuropeptides such as Tachykinins, Substance P, Substance K, and the like as well as calcitonin gene-related peptides. The use of such peptides for clinical applications has, however, been hampered by several problematic issues including deleterious side effects. Substance P, for example, is a known mediator of pain impulses and its effects on wound healing have been known for several years. However, Substance P has also been shown to stimulate neurons to release factors that recruit inflammatory cytokines and neutrophils to the site of a wound, thereby causing pain and inflammation.

Therefore, the use of peptides or growth factors and their analogs as therapeutic agents for wound healing can be problematic for a number of reasons, including efficacy, cost, and deleterious side effects such as inflammation. Information relevant to attempts to address one or more of these problems can be found in the following references: U.S. Pat. No. 7,105,481, U.S. Patent Application No. 2007/0021342, and U.S. Patent Application No. 2007/0154448. However, each one of these references suffers from one or more of the following disadvantages:

1. the requirement for expression of a polynucleotide containing the nucleotide sequence encoding the protein, which can complicate production and significantly increase costs;

2. the requirement for purification of expressed proteins from the other proteins of the host cell, which can complicate production and significantly increase costs;

3. administration of angiogenic growth factors without the further ability to activate phagocytes and thereby enhance efficacy or ameliorate infection or other concomitant disorders;

4. administration of angiogenic growth factors without the further ability to reduce inflammation, thereby reducing deleterious side effects; and 5. administration of a peptide which can stimulate the release of factors that recruit inflammatory cytokines and neutrophils to the site of a wound, causing pain and inflammation.

Therefore, in light of the available treatments for promoting wound healing by stimulating angiogenesis, there is a need to provide practical, cost-effective therapies that enhance or optimize chronic wound healing without causing deleterious side effects.

SUMMARY

The present invention generally relates to peptides and treatments that facilitate wound healing. More particularly, the invention relates to peptides that can stimulate the production of beneficial pro-angiogenic cytokines, activate phagocytes, and inhibit the release of cytokines that are deleterious to wound healing. The peptides therefore can facilitate wound healing without causing deleterious side effects such as inflammation.

In accordance with one aspect of the present invention there is provided a family of therapeutic peptides that contain at least one core sequence. The peptide core sequence, which contains at least five amino acid residues, is selected from the group consisting of: Xm-N-Xn-S-Xp; Xm-Q-Xn-S-Xp; Xm-N-Xn-T-Xp; and Xm-Q-Xn-T-Xp, wherein N is asparagine, Q is glutamine, S is serine, T is threonine, X is a naturally occurring L amino acid, and m, n, and p are integers greater than or equal to zero, and therapeutically viable fragments or derivatives thereof.

Pursuant to another aspect of the invention, there is provided a composition which contains a therapeutic peptide according to the invention. In one embodiment, the composition is a peptide construct.

According to yet another aspect of the present invention, there is provided a treatment method which includes administering to a subject an effective dose of a composition containing a therapeutic peptide according to the invention. In one embodiment, the method includes regulating the release of a specific pattern of cytokine molecules in a subject, and/or and modulating the immune system of the subject, thereby promoting the process of wound healing.

In accordance with yet another aspect of the present invention, there is provided a method for stimulating angiogenesis in a subject which includes administering an effective amount of a composition according to the invention. In one embodiment, the composition is adjacent to at least one surface of an object.

Pursuant to a further aspect of the present invention, a medical device having at least one surface comprising a peptide according to the invention is provided.

The foregoing and other features and advantages of the present invention will be apparent from the following more detailed description of the particular embodiments of the invention, as illustrated in the accompanying drawings.

DETAILED DESCRIPTION

To provide a therapeutic agent with broad properties that stimulate angiogenesis, a process essential to wound healing and restoration of circulation to damaged tissues, the agent should enhance healing without inducing clinically deleterious side effects such as inflammation, and should act in concert with a phagocytic activity in order to eliminate tissue debris and attenuate bacterial infections. The peptides of the present invention can accomplish this goal by concomitantly inducing release of beneficial cytokines, inhibiting the release of deleterious cytokines and stimulating the activity of phagocytic cells. The latter activity also allows a response of the injured tissues to respond to the presence of pathogen-directed antibodies which may arise in conditions of chronic injury. Treatment with the peptides of the present invention should induce the healing process by providing a sustained endogenous elevation of an array of beneficial cytokines, in contrast to the presence of a single cytokine given exogenously.

The following description presents embodiments of the invention representing various modes contemplated for practicing the invention. This description is not to be taken in a limiting sense but is made merely for the purpose of describing the general principles of the invention, whose scope is defined by the appended claims.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of the "a" or "an" are employed to describe elements and components of the invention. This is done merely for convenience and to give a general sense of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable processes and materials are described below. All publications, patent applications, patents, and other references mentioned herein are incorporated by reference in their entirety. In case of conflict, the present specification, including definitions, will control. In addition, the materials, processes, and examples are illustrative only and not intended to be limiting.

The following definitions refer to the particular embodiments described herein and are not to be taken as limiting; the invention includes equivalents for other undescribed embodiments.

As used herein, the term "adjacent to" when referring to the location of a peptide or peptide composition relative to a surface does not necessarily mean that the peptide or composition is immediately next to the surface. There may or may not be another contiguous or non-contiguous layer, coating, material or space present between the peptide or composition described and the surface, and the surface itself can be another layer or coating.

As used herein, the term "angiogenic" when referring to a factor or agent is intended to mean an agent which stimulates the development of blood vessels or which promotes angiogenesis including without limitation endothelial cell growth, stability of blood vessels, and/or vasculogenesis and the like.

As used herein, the term "construct" when referring to a peptide is intended to mean a framework supporting one or more peptides, including without limitation a tri-lysine central framework supporting four identical peptide sequences within the same structure.

As used herein, the term "core sequence" is intended to mean a peptide having at least one of the following amino acid sequences:

$X_m$—N—$X_n$—S—$X_p$;
$X_m$—Q—$X_n$—S—$X_p$;
$X_m$—N—$X_n$—T—$X_p$; and
$X_m$—Q—$X_n$—T—$X_p$, wherein N is asparagine, Q is glutamine, S is serine, T is threonine, X is a naturally occurring L amino acid, and m, n, and p are integers greater than or equal to zero. A core peptide sequence, and fragments or derivatives thereof, therefore contains at least one of the following pairs of amino acids: N and S(N/S), Q and S (Q/S), N and T (N/T), or Q and T (Q/T).

As used herein, the term "cytokine" is intended to a messenger molecule that controls the activity of cells, including without limitation cells of the immune system. Cytokines can control cell activity through several mechanisms, including without limitation by allowing cells to communicate and alter one another's function. Nonlimiting examples of cytokines include immunoregulatory proteins such as interleukins and interferons, which are secreted by cells of the immune system and can affect the immune response.

As used herein, the term "deleterious cytokine" is intended to mean a cytokine capable of producing one or more effects that may be deleterious with respect to treatment, including without limitation inflammation resulting from increased levels of IL-8 or ICAM-1.

As used herein, the term "deleterious side effect" is intended to mean a side effect which can be deleterious with respect to treatment, including without limitation inflammation.

As used herein, the term "effective" or "therapeutically effective" amount refers to an amount of agent effective to accelerate or otherwise improve wound healing or systemic blood circulation in a subject, or prevent recurrence of an ulcer in a subject. A therapeutic dose is a dose which exhibits a therapeutic effect on the subject.

As used herein, the term "pro-angiogenic" is intended to mean a substance or agent that stimulates or otherwise enhances angiogenesis.

As used herein, the term "stimulant" is intended to mean an agent that produces a temporary increase of the functional activity or efficiency of an organism or any of its parts, including without limitation a synthetic drug or naturally occurring substance such as adrenaline.

As used herein, the term "stimulate" or "stimulating" is intended to mean to excite to activity or growth, or to greater activity.

As used herein, the term "subject" is intended to mean one that is acted on during the course of treatment, including without limitation a human or non-human individual awaiting or under medical care or treatment.

As used herein, the term "therapeutic" when referring to a substance or treatment is intended to mean a substance or treatment concerned with providing or assisting in a cure for, or ameliorating the symptoms of, a bodily dysfunction such as that caused by disease or injury.

As used herein, the term "treatment" refers to both therapeutic treatment and prophylactic or preventative measures. Those in need of treatment include those already with a disorder as well as those in which the disorder is to be prevented.

As used herein, the term "wound healing" refers to a condition that would benefit from treatment with one or more embodiments of the present invention, The present invention generally relates to synthetic peptides that can induce release of bioactive agents that are essential for stimulation of angiogenesis. More particularly, the present invention relates to a family of synthetic peptides capable of inducing the release of beneficial cytokines which can therapeutically stimulate wound healing and respond to the presence of pathogen-directed antibodies without inducing deleterious side effects. Peptide embodiments of the present invention can stimulate the release of PDGF-BB, a pro-angiogenic cytokine, and inhibit the release of the inflammatory cytokine IL-8 that recruits neutrophils. Because neutrophils are responsible for most of the inflammatory response in injured tissue, the down-regulation of IL-8 provided by this invention is beneficial for tissue repair. In addition, the peptides can inhibit release of ICAM-1, which stimulates release of the integrins to which neutrophils bind. These effects minimize inflammation at the site of injury while stimulating the healing process. The concomitant up-regulation of PDGF-BB release, which is the key cytokine for angiogenesis, and down-regulation of IL-8 and ICAM-1 release provides favorable conditions for initiation of healing.

Furthermore, selective cross-linking of cell-surface receptors by a multivalent structure incorporating at least one peptide embodiment of the present invention may attenuate bacterial infections by stimulating activity of phagocytic cells that are recruited to the injured or infected tissue. Phagocytic cells respond to the presence of bacterial cells containing lipopolysaccharide (LPS) on their surface by engulfing the cells into phagocytic vacuoles and digesting the bacterial cells. In addition, the phagocytic cells respond to the presence of antibodies directed toward—and bound to—a pathogen such as a bacterial cell, fungal cell or virus.

FIG. 1 illustrates a working model of the molecular structure of one embodiment of a multivalent immunoregulatory peptide construct 10 according to the invention. The construct 10 can be synthesized with multiple arms 1, including without limitation two, three, four, and eight or more arms 1, using the same core peptide sequence 2 on all four arms or with two or more different sequences. The length of the spacer 3 between the central framework 4 of the construct and the core peptide sequence 2 determines the length of the arm 1. The arms 1 illustrated in FIG. 1, having a sequence of five or six amino acids, can be about 3±0.5 nm in length depending on conformation (approximately 7 nm across the molecule), for example. Cell-surface domains of known receptor proteins are correspondingly about 3 nm to about 4 nm in diameter. This distance can be adjusted by increasing or decreasing the length of the linker. Therefore, cross-linking of receptors can be achieved with such an embodiment. The multidimensional nature of the structure illustrated in FIG. 1 was obtained using standard molecular modeling techniques.

EXAMPLES

Example 1

Peptide Design and Synthesis

A screen of peptide sequences identified one set of sequences of interest. The corresponding peptides were synthesized by solid-phase methods using standard Fmoc side chain protection. Branched peptides were constructed on a central tri-lysine framework, which allows four identical sequences within the same structure. A $(Gly)_3$-Ser (GGGS, SEQ ID NO:3) linker sequence was included to distance the active sequence from the central framework. Distances between the active sequences can be adjusted by decreasing or increasing the length of the linker, including without limitation the use of two linkers in tandem (GGGSGGGS, SEQ ID NO:4) or by inserting any inert linker such as polyethylene glycol (PEG) of a variable length. The branched structure was designed to have enhanced activity by causing receptor clustering (cross-linking) on the surface of responsive cells.

The peptides were synthesized on PAL-PEG-polystyrene resin (Applied Biosystems, Foster City, Calif.) utilizing Fmoc (9-fluorenylmethoxycarbonyl)-protected amino acids and a Milligen Biosearch 9050+ continuous flow peptide synthesizer (Millipore Corporation, Billerica, Mass.).

The C-terminus of the central framework is typically a lysine (K) residue. However, the C-terminus can be modified to include additional C-terminal amino acids such as a cysteine residue, to which tags such as fluorescent groups can be added, or an ε-biotinyl-N-lysine (biotinyl-K) residue useful for subsequent purification processes. In addition, an amino acid such as β-alanine (βA) or tryptophan (W) can be inserted between the added C-terminal amino acid and the C-terminal lysine residue of the central framework in order to provide a spacer or a means to determine concentration by absorbance. Non-limiting examples of such modified C-terminal lysine residues on the central framework include K-βA-C and K-W-biotinyl-K, respectively. Furthermore, additional lysine residues can be added to either one or both of the α- and ε-amino groups of a modified C-terminal lysine on the central framework to yield, for example, $(K)_2K$, $(K)_2K$-βA-C or $(K)_2K$-W-biotinyl-K, thereby forming branched structures in which the α- and ε-amino groups are available for extension.

The lysine residues used at the branch points are incorporated with Fmoc protection on both the α- and ε-amino groups, so that both become available for amide bond formation after the standard deprotection reaction with piperidine. A dansyl group (or other fluorescent tag) may be incorporated by reaction with the thiol group on the C-terminal cysteine residue using 5-((((2 iodoacetyl)amino)ethyl)amino)naphthalene-1-sulfonic acid (1,5-IAEDANS) following a standard protocol for thiol-reactive probes (Invitrogen Corp., Carlsbad, Calif.). Biotin is attached to lysine through an amide linkage to the side chain amino group which, because of its high affinity with streptavidin, provides a means to retrieve the peptide with associated proteins from reaction mixtures in order to study the interaction of the peptide with cellular components.

The peptides were built attached to a solid-phase resin, which was chosen such that when the peptide is cleaved from the resin, the carboxyl group at the C-terminus of the peptide is released as the amide. Each of the four amino groups of the tri-lysine central framework was extended by addition of the linker sequence, GGGS (SEQ ID NO:3), followed by the active core peptide sequence.

After cleavage from the resin bed, the product can be substantially or completely purified by HPLC on a preparative Jupiter Proteo C12 column (21.2 mm×250 mm) (Phenomenex, Inc., Torrance, Calif.) using a gradient from 8% to 18% acetonitrile in water containing 10 mM trifluoroacetic acid (TFA). The purity of the final peptide product was confirmed by mass spectroscopy performed using a Voyager DE STR mass spectrometer (Applied Biosystems, Foster City, Calif.). HPLC-purified peptide is dried under vacuum, dissolved in sterile phosphate buffered saline, pH 7.2 (PBS) and passed through a gel filtration column of Sephadex G 15 or G 25 (1×48 cm for small samples) to separate TFA from the peptide. The column is then eluted with sterile PBS.

Alternatively, the product is purified by use of a C18 reverse-phase cartridge, ion exchange chromatography, and gel filtration chromatography to remove side products of synthesis. Concentration can be determined by absorbance of the fluorophore (e.g., dansyl group, extinction coefficient, $\epsilon_{mM}$=5.7 $cm^{-1}$ at 336 nm), absorbance of the peptide bond at 210 nm ($\epsilon_{mg/ml}$≈31 $cm^{-1}$), absorbance of aromatic amino acids (e.g., tryptophan, $\epsilon_{mM}$=5.6 $cm^{-1}$ at 280 nm) in the peptide (when present) and/or absorbance of the bicinchoninic acid reagent (Pierce Biotechnology, Rockford, Ill.). The peptide solutions can be adjusted to the desired concentration and filter-sterilized prior to use.

Example 2

Core Peptides WNSTL (SEQ ID NO:1) and NQHTPR (SEQ ID NO:2)

The peptides tryptophan-asparagine-serine-threonine-leucine (WNSTL, SEQ ID NO:1) and asparagine-glutamine-histidine-threonine-proline-arginine (NQHTPR, SEQ ID NO:2) were identified through a screen of peptide sequences as potentially of interest. The sequences were synthesized on a tri-lysine core according to Posnett et al., J. Biol. Chem., 263: 1719-25, 1988, with a $(glycine)_3$-serine (GGGS, SEQ ID NO:3) linker included with the sequence to extend the active peptide away from the core.

Figures 1, 3:
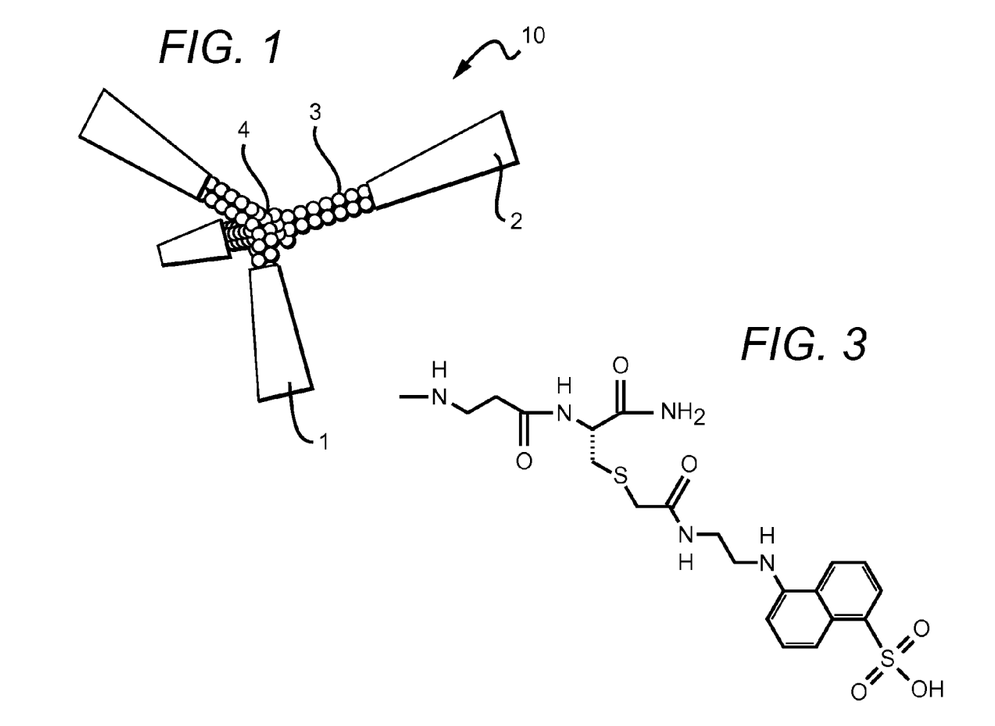
FIG. 1 illustrates a molecular structure of one embodiment of the present invention, a multivalent peptide construct containing four peptides according to the invention, each of which is linked to a central core structure via a linker sequence.
FIG. 3 illustrates the structure of a reporter tag that can be added to a peptide according to the present invention, a C-terminal extension containing a fluorescent dansyl group.
Figure 2A:
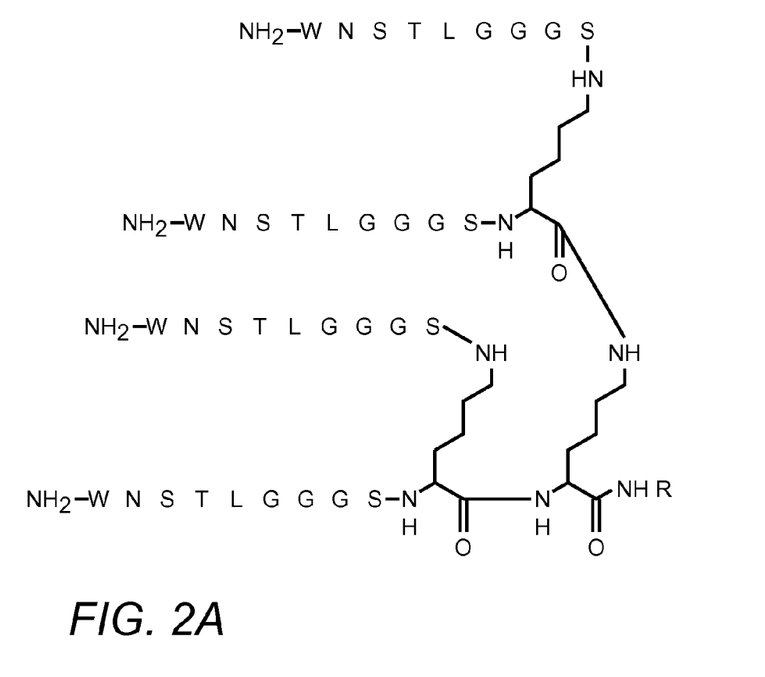
FIG. 2A illustrates the chemical structure of a peptide construct according to one embodiment of the present invention, the construct SynGia™H1B containing four copies of the core sequence WNSTL (SEQ ID NO:1) linked to a branched central framework structure.
Figure 2B:
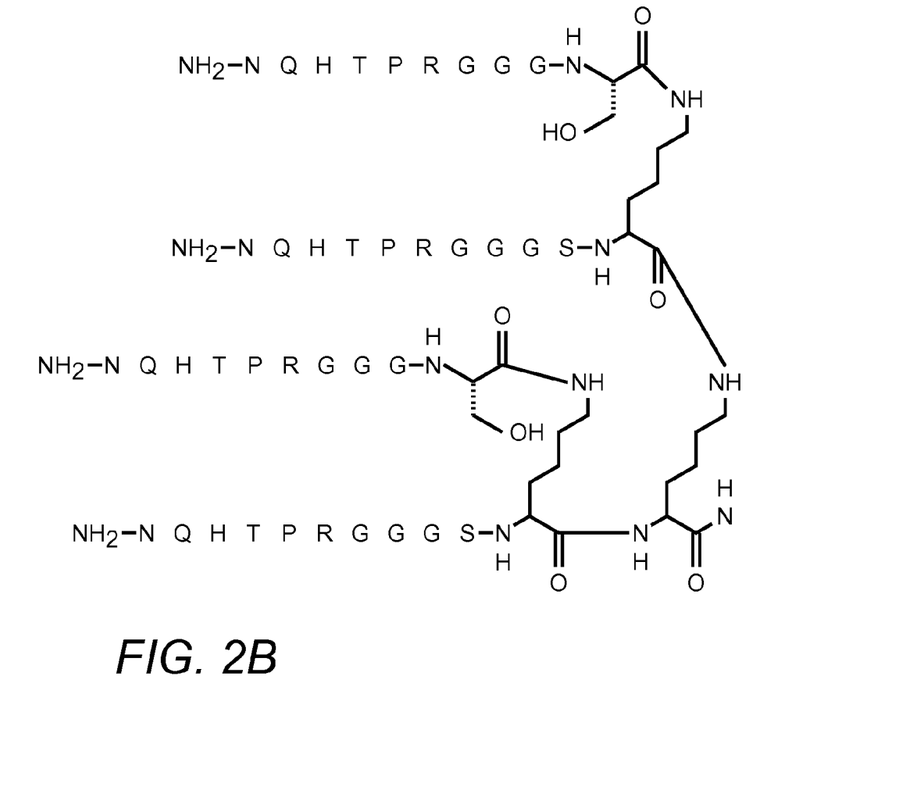
FIG. 2B illustrates the chemical structure of a peptide construct according to one embodiment of the present invention, the construct SynGia™6D containing four copies of the core sequence NQHTPR (SEQ ID NO:2) linked to a branched central framework.

FIGS. 2A-2B illustrate the chemical structure of these two embodiments of the invention. In these embodiments, R=H or can be an adduct containing a fluorescent tag such as the dansyl group shown in FIG. 3. The peptide constructs illustrated contain four identical sequences, each of which is connected to a branched central tri-lysine framework via a $(Gly)_3$Ser (GGGS, SEQ ID NO:3) linker sequence. FIG. 2A is a branched peptide construct according to one embodiment of the invention, designated SynGia™H1B, which contains four copies of the core sequence containing peptide WNSTL (SEQ ID NO:1). The peptide embodiment containing R=H has a molecular mass of 3,841.16 Daltons.

FIG. 2B illustrates the structure of the construct containing the N-terminal sequence NQHTPR (SEQ ID NO:2), designated SynGia™6D. The peptide embodiment containing R=H has a molecular mass of 4,543.89. In another embodiment, a C-terminal extension containing β-alanine, cysteine and a dansyl tag, as shown in FIG. 3, is covalently added to the construct illustrated in FIG. 2B, resulting in a peptide having a molecular mass of 4,850.23 Daltons.

Example 3

Regulation of Cytokine Release

To determine whether the peptides regulate induction or inhibition of release of cytokines, cultured peripheral blood mononuclear cells (PBMCs) were treated with one peptide embodiment of the invention and, after 4 hour incubation, the medium was collected and assayed for changes in the amounts of 40 different cytokines. The WNSTL (SEQ ID NO:1) peptide construct SynGia™H1B, illustrated in FIG. 2A, was added at a concentration of 100 nM in each of the assays. The PBMC cultures were established with cells from Cellular Technologies, Ltd. (Shaker Heights, Ohio). Approximately 3 million cells of frozen human PBMCs are thawed at 37° C. and transferred to a 50 ml conical tube where 8 ml of wash medium are added slowly. Then an additional 8 ml are added and swirled to mix. The cells are then centrifuged at 330 g for 10 min, the supernatant is removed and the pellet is resuspended in 10 ml wash medium and centrifuged as above. The washed cells are then resuspended in RPMI 1640 medium containing 10% FBS to about 6 million cells per ml and 100 μl of the suspension are added into each well of a 96 well microtiter plate and incubated overnight at 37° C. in humidified 5% $CO_2$. After 24 hr, the medium is replaced with 200 μl fresh RPMI 1640 medium containing 10% FBS and incubated at 37° C. in humidified 5% $CO_2$ for 2 days. For the data shown in Table 1, an aliquot of the peptide construct was added to samples in duplicate at a final concentration of 5 nM or 100 nM and incubated at 37° C. in humidified 5% $CO_2$ for 4 hr. For other experiments (data not included), the incubation was continued for 24 hr. The medium was then removed and stored at 80° C. The samples are analyzed for production of cytokines. One set of control cells was not treated with an experimental agent. A second set of control cells was treated with LPS, the agent commonly used to induce production of a variety of inflammatory cytokines. The positive control for inflammation provided by this second set of control cells is essential to ensure that the peptides do not produce an unregulated inflammatory response.

Assays of cytokine levels in samples of culture media were performed using methods developed by RayBiotech, Inc. (Norcross, Ga.). In this technology, membrane arrays of antibodies against cytokines are incubated with samples of media. After washing, the array is incubated with a cocktail of all antibodies tagged with biotin. The membrane is then washed free of unbound antibodies and incubated with streptavidin labeled with a fluorescent dye. After a final wash, the membrane arrays are read in a fluorescence detector and the intensities of the spots quantitated to obtain relative values.

TABLES 1-2 list a number of cytokines whose concentrations in a medium of PBMC cultures can be altered as the result of treatment of the cells with peptide embodiments of the present invention. The cytokines thus affected include without limitation:

Eotaxin (chemoattractant, induces substantial accumulation of eosinophils);
Eotaxin-2 (induces chemotaxis of eosinophils and basophils, release of histamine);
GCSF (granulocyte colony stimulating factor, growth factor);
ICAM-1 (intercellular adhesion molecule-1, binds to integrins, human rhinovirus receptor);
IL-1β (Interleukin 1β, a mediator of inflammatory reactions);
IL-4 (promotes proliferation and differentiation of B-cells and inhibits production of inflammatory cytokines such as IL-1, IL-6 and TNF-α);
IL-6SR (soluble receptor for IL-6);
IL-7 (stimulates proliferation of precursor B and T cells);
IL-8 (chemoattractant and activator of neutrophils);
IL-10 (inhibits synthesis of inflammatory cytokines such as INF-γ, IL-2 and TNF-β);
IL-11 (induces inflammatory responses, promotes immune responses);
IL-12 (contains subunits of 40 and 70 kDa, activates NK-cells and stimulates proliferation of lymphoblasts);
IL-15 (has many of the same properties as IL-2, may contribute to T-cell mediated immune responses);
IL-16 (chemoattractant and activator for cells that express CD4);
IL-17 (functions as a mediator of angiogenesis that stimulates migration of vascular endothelial cells and cord formation and regulates production of a variety of growth factors promoting angiogenesis);
INF-γ (Interferon-gamma, has antiviral, immunoregulatory and anti-tumor properties);
MCP-1,2 (monocyte chemotactic proteins):
M-CSF (induces proliferation and stimulates monocytes and macrophages);
MIG (chemoattractant for stimulated T cells but not active on neutrophils or monocytes);
MIP-1b (macrophage inflammatory protein, involved in cell activation of granulocytes and killer cells);
PDGF-BB (platelet-derived growth factor, BB homodimer);
RANTES (regulated on activation, normal T cell expressed, and secreted; chemotactic for T cells);
sTNF RI, RII (soluble forms of receptor RI or RII for tumor necrosis factor (TNF));
TIMP-2 (tissue inhibitor of metalloproteinases of the extracellular matrix); and
TNF-β (promotes the proliferation of fibroblasts and is involved in wound healing).

Table 1 contains data showing cytokines that are released at a significantly higher or lower rate (compared to untreated controls) during a 4-hour incubation of PBMCs with the branched peptide construct SynGia™H1B in the presence of serum. One set of control samples was not treated with peptide and a second set of control samples was treated with lipopolysaccharide (LPS) in the absence of peptide. SynGia™H1B, whose structure is illustrated in FIG. 2A, contains the core peptide sequence WNSTL (SEQ ID NO:1). Among the cytokines that are induced to more than two-fold higher concentrations as a result of incubation with SynGia™H1B are PDGF-BB, IL-1β, IL-4, IL-1, IL-12 and RANTES. In contrast, several cytokines show more than a two-fold decrease in concentration as compared to untreated control samples with this peptide. The decrease in IL-8 concentration in the peptide-treated sample, as compared with the amount of IL-8 in the sample treated with the prototypical inflammatory agent LPS, is particularly notable. Furthermore, when compared to untreated control samples, the peptides did not induce a change in the amount of the inflammatory cytokine IL-6. However, IL-6 levels were significantly elevated in samples treated with LPS in the absence of peptide. In one experiment, for example, the peptide treated sample had a relative IL-6 concentration of 93, the untreated control sample, 98, and the LPS-treated sample (in the absence of peptide), 5,879. Because the concentration of IL-6 in the peptide treated sample was not significantly different from the untreated control sample, the data for IL-6 are not included in Tables 1 or 2. The increase in the pro-angiogenic PDGF-BB and the decrease in the inflammatory IL-8, without concomitant stimulation of inflammation, are of particular importance with respect to wound healing.

TABLE 1

Relative Cytokine Concentration after Incubation of PBMCs in Serum with Peptide Construct SynGia ™H1B Containing the Core Sequence WNSTL (SEQ ID NO: 1).

| Cytokine* | WNSTL (SEQ ID NO: 1) | Untreated (control) | LPS (control) |
|---|---|---|---|
| Increased: | | | |
| PDGF-BB | 159 | 43 | 56 |
| IL-1β | 120 | 44 | 48 |
| IL-4 | 97 | 30 | 49 |
| IL-11 | 49 | 17 | 27 |
| IL-12p40 | 228 | 50 | 46 |
| IL-12p70 | 131 | 90 | 89 |
| RANTES | 145 | 60 | 114 |
| S TNF RI | 78 | 42 | 58 |
| Decreased: | | | |
| IL-7 | 93 | 154 | 178 |
| IL-8 | 144 | 417 | 840 |
| IL-10 | 43 | 101 | 218 |
| Eotaxin-2 | 109 | 194 | 470 |
| GCSF | 50 | 108 | 120 |
| ICAM-1 | 44 | 58 | 53 |
| INF-γ | 103 | 134 | 158 |
| IL-6SR | 32 | 52 | 52 |
| TIMP-2 | 25 | 58 | 92 |
| MCP-1 | 968 | 1464 | 1844 |

Relative cytokine concentration data for the peptide construct SynGia™6D is similarly outlined in Table 2. SynGia™6D, whose structure is illustrated in FIG. 2B, contains the core peptide sequence NQHTPR (SEQ ID NO:2). Cytokines were again observed at significantly higher or lower concentrations (relative to controls) after a 4-hour incubation with the branched SynGia™6D construct. The data in Table 2 show that, although the overall pattern of cytokine response to this peptide is somewhat different from that of SynGia™H1B shown in Table 1, it similarly induces a higher amount of PDGF and a lower amount of IL-8.

Toxicity of the peptide in vivo can be tested by injection of a peptide into animal subjects, including without limitation mice. The peptides can be administered in a number of ways, including without limitation by injection (intravenously, subcutaneously, intramuscularly or intraperitoneally), topically (transmucosally, transbuccally, or transdermally) and/or orally (liquid, tablet or capsule). In preliminary studies on mice, no adverse effects of the peptide on the growth rate of the animals have been observed after injection of an effective dose on alternate days for 1 month (data not shown).

TABLE 2

Relative Cytokine Concentration after Incubation of PBMCs in Serum with Peptide Construct SynGia ™6D Containing the Core Sequence NQHTPR (SEQ ID NO: 2).

| Cytokine | NQHTPR (SEQ ID NO: 2) | Untreated (control) |
|---|---|---|
| Increased: | | |
| PDGF-BB | 84 | 43 |
| Eotaxin | 57 | 32 |
| Eotaxin-2 | 310 | 193 |
| IL-15 | 146 | 97 |
| IL-16 | 8 | 1 |
| IL-17 | 14 | 5 |
| MCP-2 | 90 | 56 |
| M-CSF | 116 | 44 |
| MIG | 100 | 54 |
| TNF-β | 84 | 38 |
| sTNF RII | 26 | 8 |
| TIMP-2 | 110 | 58 |
| Decreased: | | |
| IL-8 | 261 | 417 |
| MIP-1b | 777 | 1172 |

Example 4

Pro-angiogenic Activity of Peptides

Tumors require vascularization to obtain nutrients to support growth. Therefore, stimulation of growth of a tumor in response to administration of a construct of this invention is an indication of angiogenesis. For this example, a xenograph model system with the nude mouse (nu/nu) was used to determine the effect of peptide on growth of 786-O human renal cell adenocarcinoma cell line injected into the flank of a mouse so as to induce a tumor. After the tumor was established, peptide was injected subcutaneously on alternate days. The weight of the tumor was estimated by calculation of the volume.

Figure 4:
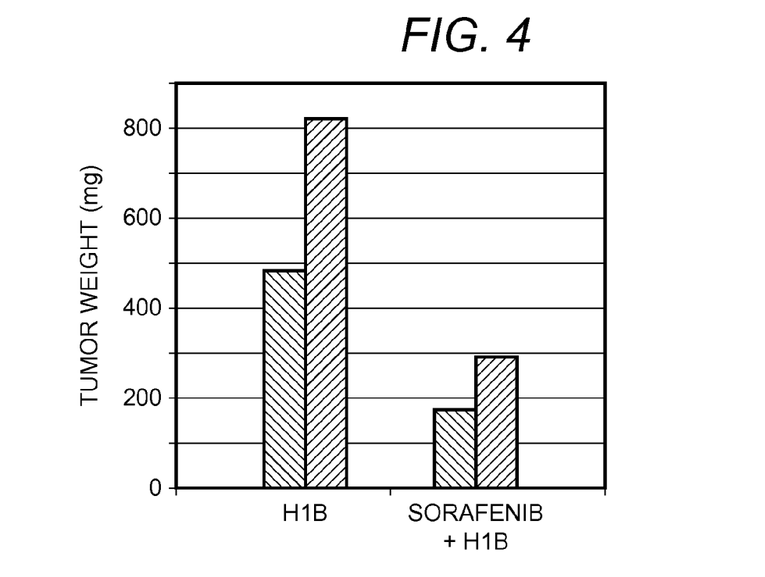
FIG. 4 is a bar graph of data illustrating the stimulation of growth of a tumor as the result of pro-angiogenic activity by one embodiment of the present invention, the peptide construct SynGia™H1B containing the core sequence WNSTL (SEQ ID NO:1) as illustrated in FIG. 2A.

FIG. 4 illustrates data resulting from assays for pro-angiogenic activity for one embodiment of the invention. The bar graph in FIG. 4 shows the average weight of the tumor in mice treated with the peptide construct SynGia™H1B containing four copies of the core peptide WNSTL (SEQ ID NO:1)) at a dose of 0.05 nmole/gm as compared with a control group. The peptide was also assayed in combination with Sorafenib, an anti-angiogenic drug. The results shown in FIG. 4 indicate that growth of the tumor was significantly enhanced, by a factor of 1.7, over the control in mice to which the construct SynGia™H1B was administered. The drug Sorafenib, an inhibitor of angiogenesis, strongly (but not completely) inhibited the effect of the peptide.

Example 5

Devices or Materials Containing Core Peptides

The peptides of the present invention may also be deposited to provide an appropriate coating to a surface, including without limitation a bioactive surface or an inert, non-biological surfaces of a device or materials designed for implantation. The peptides can thus promote healing around the implanted materials in order to achieve vascularization without scarring. They could similarly be used in other in vitro or in vivo applications, including without limitation with embedded sensors.

The embodiments and examples set forth herein were presented in order to best explain the present invention and its practical application and to thereby enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above without departing from the spirit and scope of the forthcoming claims. Although the examples herein disclose the therapeutic efficacy of the peptides of the present invention with respect to wound healing, for example, the peptides may also be useful for restoration of circulation generally, including circulation compromised by chronic conditions such as diabetes, circulation to damaged tissues, and other similar disorders. Furthermore, the use of larger peptides containing active core sequences could potentially enhance the therapeutic benefits disclosed herein.

BACKGROUND REFERENCES

Arici A (2002) Local cytokines in endometrial tissue: the role of interleukin-8 in the pathogenesis of endometriosis. Ann NY Acad Sci 955: 101-109.

Baggiolini M, Loetscher P, Moser B (1995) Interleukin-8 and the chemokine family. Int J Immunopharmacol 17: 103-108.

Barja-Fidalgo C, Coelho A L J, Saldanha-Gama R, Helal-Neto E, Mariano-Oliveira A, de Freitas M S (2005) Disintegrins: integrin selective ligands with activate integrin-coupled signaling and modulate leukocyte functions. Braz J Med Biol Res 38: 1513-1520.

Delgado A V, McManus A T, Chambers J P (2005) Exogenous administration of Substance P enhances wound healing in a novel skin-injury model. Exptl Biol Med 230: 271-280.

Etzoni A (1999) Integrins: the glue of life. Lancet 353: 341-343.

Li W W and Li V W (2003a) The biology of PDGF and other growth factors in wound neovascularization. Contempory Surgery, Supplement, November, 12-18.

Li W W and Li V W (2003b) Therapeutic angiogenesis: using growth factors to restore circulation in damaged tissues. Contempory Surgery, Supplement, November, 19-25.

Li V W and Li W W (2003c) Angiogenic therapy for chronic wounds: the clinical experience with Becaplermin. Contempory Surgery, Supplement, November, 26-32.

Li W W, Tsakayannis D and Li V W (2003) Angiogenesis: a control point for normal and delayed wound healing. Contempory Surgery, Supplement, November, 5-11.

O'Shea J J, Ma A, Lipsky P (2002) Cytokines and autoimmunity. Nature Rev Immunol 2: 37-45.

We claim:

1. A therapeutic peptide consisting of a construct and at least two arms, the construct having a central framework and each arm consisting of a core sequence linked to the central framework via a linker sequence, each core sequence is the same or different and is selected from the group consisting of: WNSTL (SEQ ID NO:1), NQHTPR (SEQ ID NO:2), WNSTY (SEQ ID NO:5), YNSTL (SEQ ID NO:6), YQPSL (SEQ ID NO:7), and VQATQS (SEQ ID NO:8).

2. The therapeutic peptide of claim 1, wherein the central framework is a tri-lysine framework and the linker sequence is GGGS (SEQ ID NO:3) or GGGSGGGS (SEQ ID NO:4).

3. The therapeutic peptide of claim 1, wherein the core sequence is WNSTL (SEQ ID NO:1).

4. The therapeutic peptide of claim 3, wherein the linker sequence is GGGS (SEQ ID NO:3) or GGGSGGGS (SEQ ID NO:4), and the therapeutic peptide is branched having four core sequences each being WNSTL (SEQ ID NO:1).

5. A pro-angiogenic composition comprising at least one therapeutic peptide according to claim 1 and a pharmaceutically acceptable carrier.

6. The composition of claim 5, wherein the therapeutic peptide comprises three or four arms that are the same.

7. The composition of claim 6, wherein the linker sequence is GGGS (SEQ ID NO:3) or GGGSGGGS (SEQ ID NO:4) and the construct is branched.

8. A wound treatment method comprising administering an effective dose of the composition of claim 5 to a subject having a wound, wherein the composition is administered in an amount sufficient to stimulate the production of at least one therapeutically beneficial cytokine and/or inhibits at least one therapeutically deleterious cytokine or to modulate the immune system of the subject, thereby promoting the process of wound healing.

9. The method of claim 8, wherein the at least one beneficial cytokine is PDGF-BB and the least one deleterious cytokine is cytokine is IL-8.

10. A method for stimulating angiogenesis in a subject, comprising administering to a subject and effective amount of a composition according to claim 5.

11. The treatment method of claim 10, wherein the composition administered is on a medical device.

12. A therapeutic peptide consisting of an amino acid sequence selected from the group consisting of WNSTL (SEQ ID NO:1), NQHTPR (SEQ ID NO:2), WNSTY (SEQ ID NO:5), YNSTL (SEQ ID NO:6), YQPSL (SEQ ID NO:7), and VQATQS (SEQ ID NO:8).

13. The therapeutic peptide of claim 12, wherein the peptide is VQATQS (SEQ ID NO:8).

14. The therapeutic peptide of claim 12, wherein the peptide is WNSTY (SEQ ID NO:5).

15. The therapeutic peptide of claim 12, wherein the peptide is YNSTL (SEQ ID NO:6).

16. The therapeutic peptide of claim 12, wherein the peptide is YQPSL (SEQ ID NO:7).

17. The therapeutic peptide of claim 12, wherein the peptide is NQHTPR (SEQ ID NO:2).

18. The therapeutic peptide of claim 12, wherein the peptide is WNSTL (SEQ ID NO:1).

19. A therapeutic branched peptide consisting of a tri-lysine core and four peptides, each peptide consisting of the sequence WNSTL (SEQ ID NO:1) linked to the tri-lysine core via at least one linker sequence consisting of GGGS (SEQ ID NO:3).

20. A therapeutic branched peptide consisting of a tri-lysine core and four peptides, each peptide consisting of the sequence NQHTPR (SEQ ID NO:2) linked to the tri-lysine core via at least one linker sequence consisting of GGGS (SEQ ID NO:3).

21. The therapeutic peptide of claim 1, wherein the core sequence is VQATQS (SEQ ID NO:8).

22. The therapeutic peptide of claim 1, wherein the core sequence is WNSTY (SEQ ID NO:5).

23. The therapeutic peptide of claim 1, wherein the core sequence is YNSTL (SEQ ID NO:6).

24. The therapeutic peptide of claim 1, wherein the core sequence is YQPSL (SEQ ID NO:7).

25. The therapeutic peptide of claim 1, wherein the core sequence is NQHTPR (SEQ ID NO:2).

* * * * *